(12) United States Patent
Muraki

(10) Patent No.: US 6,999,813 B2
(45) Date of Patent: Feb. 14, 2006

(54) BIOMEDICAL SIGNAL PROCESSOR AND METHOD OF CONTROLLING BIOMEDICAL SIGNAL PROCESSOR

(75) Inventor: Yoshiya Muraki, Hasuda (JP)

(73) Assignee: Fukuda Denshi Co., Ltd., Tokyo (JP)

( * ) Notice: Subject to any disclaimer, the term of this patent is extended or adjusted under 35 U.S.C. 154(b) by 450 days.

(21) Appl. No.: 10/281,405

(22) Filed: Oct. 25, 2002

(65) Prior Publication Data

US 2004/0082869 A1    Apr. 29, 2004

(51) Int. Cl.
*A61B 5/0402*    (2006.01)

(52) U.S. Cl. ..................................... 600/523

(58) Field of Classification Search ......... 600/508–525
See application file for complete search history.

(56) References Cited

FOREIGN PATENT DOCUMENTS

JP    2002-125944    5/2002

*Primary Examiner*—Scott M. Getzow
(74) *Attorney, Agent, or Firm*—Merchant & Gould P.C.

(57) ABSTRACT

To disclose a biomedical signal processor with a simple configuration and a minimum space capable of confirming an operating condition and a signal collection state of the biomedical signal processor such as an electrocardiograph. As an example of the biomedical signal processor according to the present invention, a Holter electrocardiograph supplies biomedical signals to a light-emitting element (LED) 30 and applies a bias supply voltage from a power supply section 80 to the LED 30. By setting a bias voltage to a voltage so that a level of a minimum supply voltage to the LED 30 becomes a positive potential when electrocardiogram signals are input to an input amplification section 10, the LED 30 turns OFF when power is turned OFF, becomes half-lit when power is turned ON and its luminescence intensity is variable when signals are collected normally, making it possible to easily check a state of the apparatus.

4 Claims, 3 Drawing Sheets

BIOMEDICAL SIGNAL PROCESSOR AND METHOD OF CONTROLLING BIOMEDICAL SIGNAL PROCESSOR

FIELD OF THE INVENTION

The present invention relates to a biomedical signal processor provided with an input amplification section for taking in and amplifying biomedical signals from a detection section that detects those biomedical signals and light-emitting means, and a method of controlling the same, and more particularly, to a biomedical signal processor suitable for a portable type apparatus that collects electrocardiograms and a method of controlling the same.

BACKGROUND OF THE INVENTION

Conventionally, a medical telemetery transmitter is widely used as a biomedical signal processor that collects biomedical signals such as electrocardiograms of an examinee and transmits the collected biomedical signals by radio to a monitor device, etc. installed in a nurse center, etc. This type of medical telemetery transmitter is designed to attach biomedical electrodes to predetermined parts on the surface of the skin of the examinee and transmit the biomedical signals collected from the biomedical electrodes by radio.

For this type of apparatus, it is necessary to confirm whether the biomedical electrodes are attached correctly or not. For this confirmation, the apparatus may be provided with a display device to display electrocardiogram waveforms collected from the electrocardiogram electrodes as in the case of a general electrocardiograph, but since a reduction in size and weight of such a medical telemetery transmitter is the first requirement to minimize burdens on the examinee, a configuration including a display device which will result in an increase of the size of the device is not acceptable in practice.

As a result, in order to check the electrode connection state, it is necessary to go to a place distant from the telemetery transmitter where the display device of the receiver is installed and check the display screen, which is quite troublesome.

SUMMARY OF THE INVENTION

The present invention has been achieved to solve the above described problems and it is an object of the present invention to provide a biomedical signal processor capable of checking the connection state of a biomedical signal detection section such as electrocardiogram electrodes, for example, a Holter electrocardiograph, and a method of controlling the biomedical signal processor. As means for attaining the above object, the present invention adopts, for example, the following configurations.

That is, the present invention provides a biomedical signal processor including a power supply section that supplies drive power to the apparatus, an input amplification section that takes in and amplifies biomedical signals from a detection section that detects those biomedical signals, bias means for applying a predetermined bias voltage to the output signal from the input amplification section, and light-emitting means for emitting light with intensity corresponding to the biomedical signals to which the bias means applies the predetermined bias voltage, characterized in that it is possible to simultaneously recognize the operating condition of the power supply section and the detection condition of the detection section from the luminescence intensity of the light-emitting means.

Furthermore, the present invention is characterized in that using, for example, electrocardiogram signals as the biomedical signals and electrocardiogram electrodes as the detection section, the bias means applies a bias voltage so that the luminescence intensity of the light-emitting means is reduced to half when no electrocardiogram signal is detected from the input amplification section.

Furthermore, the present invention provides a method of controlling a biomedical signal processor provided with an input amplification section that takes in and amplifies biomedical signals from a detection section that detects those biomedical signal and light-emitting means, comprising the steps of amplifying the input signal at the input amplification section, adding a predetermined bias voltage thereto and letting the light-emitting means emit light with intensity corresponding to the biomedical signals with the bias voltage added, characterized in that it is possible to simultaneously recognize the operating condition of the power supply section and the detection condition of the detection section from the light-emitting state of the light-emitting means.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will now be described in detail in accordance with the accompanying drawings.

The following explanation will describe a case where a biomedical signal processor of the present invention is applied to a medical telemetery apparatus that collects an electrocardiogram and transmits the electrocardiogram by radio to a monitor device, etc. as an example. However, it goes without saying that the present invention is also applicable to various types of biomedical signal processors that take in and process signals from a living body, and especially when applied to medical equipment such as a Holter electrocardiograph whose miniaturization is strongly demanded, the present invention can attain outstanding effects of operation.

Figure 1:
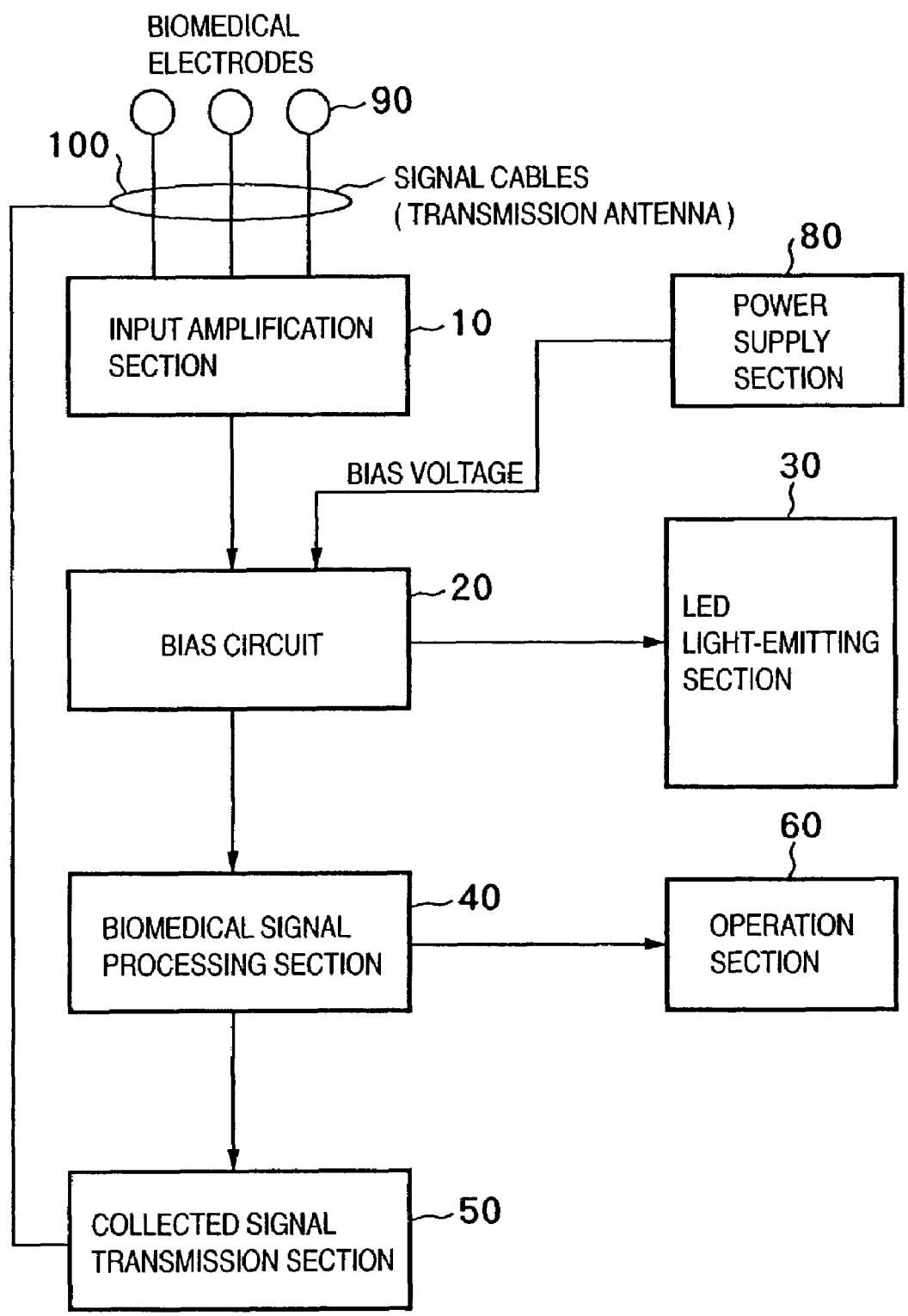
FIG. 1 is a block diagram showing a configuration of a medical telemetery apparatus according to an embodiment of the present invention.

First, with reference to FIG. 1, a configuration of a medical telemetery apparatus according to an embodiment of the present invention capable of collecting electrocardiogram signals and transmitting the signals by radio will be explained. FIG. 1 is a block diagram showing a configuration of a medical telemetery apparatus as a biomedical signal processor according to an embodiment of the present invention.

In FIG. 1, reference numeral 10 denotes an input amplification section that takes in electrocardiogram signals from biomedical electrodes 90 which are electrocardiogram electrodes attached to predetermined positions on the surface of the skin of an examinee, amplifies the input biomedical signals from the biomedical electrodes 90 and outputs to a bias circuit 20.

Reference numeral 20 denotes a bias circuit that applies a predetermined bias voltage to the electrocardiogram signals from the input amplification section 10, 30 denotes an LED light-emitting section that emits light with intensity corresponding to the signal level of the output signal from the input amplification section 10 to which the bias circuit 20 has applied the bias voltage.

Reference numeral 40 denotes a biomedical signal processing section that samples the output signal from the input amplification section 10 sent through the bias circuit 20 according to a predetermined sampling timing, converts the sampled signal to a digital signal, subjects the converted electrocardiogram signal information to predetermined signal processing such as elimination of noise components and outputs the processed information to a collected signal transmission section 50 on a time-division basis.

Reference numeral 50 denotes a collected signal transmission section that modulates the transmit information sent from the biomedical signal processing section 40, outputs and transmits by radio the modulated high frequency signal using signal cables 100 that connect the biomedical electrodes 90 and the input amplification section 10 as an antenna. Reference numeral 60 denotes an operation section and is made up of a power switch and start switch, etc.

Furthermore, reference numeral 80 denotes a power supply section that supplies drive power to the respective components of the medical telemetery apparatus according to this embodiment and supplies a predetermined bias voltage to the bias circuit 20. For example, using a converter, the power supply section converts a certain DC voltage supplied from, for example, a battery to drive voltages required for the respective components and supplies the drive voltages to the respective components.

Reference numeral 90 denotes biomedical electrodes that are attached to predetermined parts on the surface of the skin of the examinee and detects electrocardiogram signals, 100 denotes shielded signal cables that connect the biomedical electrodes 90 and input amplification section 10, and these shielded signal cables also serve as an antenna for radio transmissions from the collected signal transmission section 50 in this embodiment.

Figure 2:
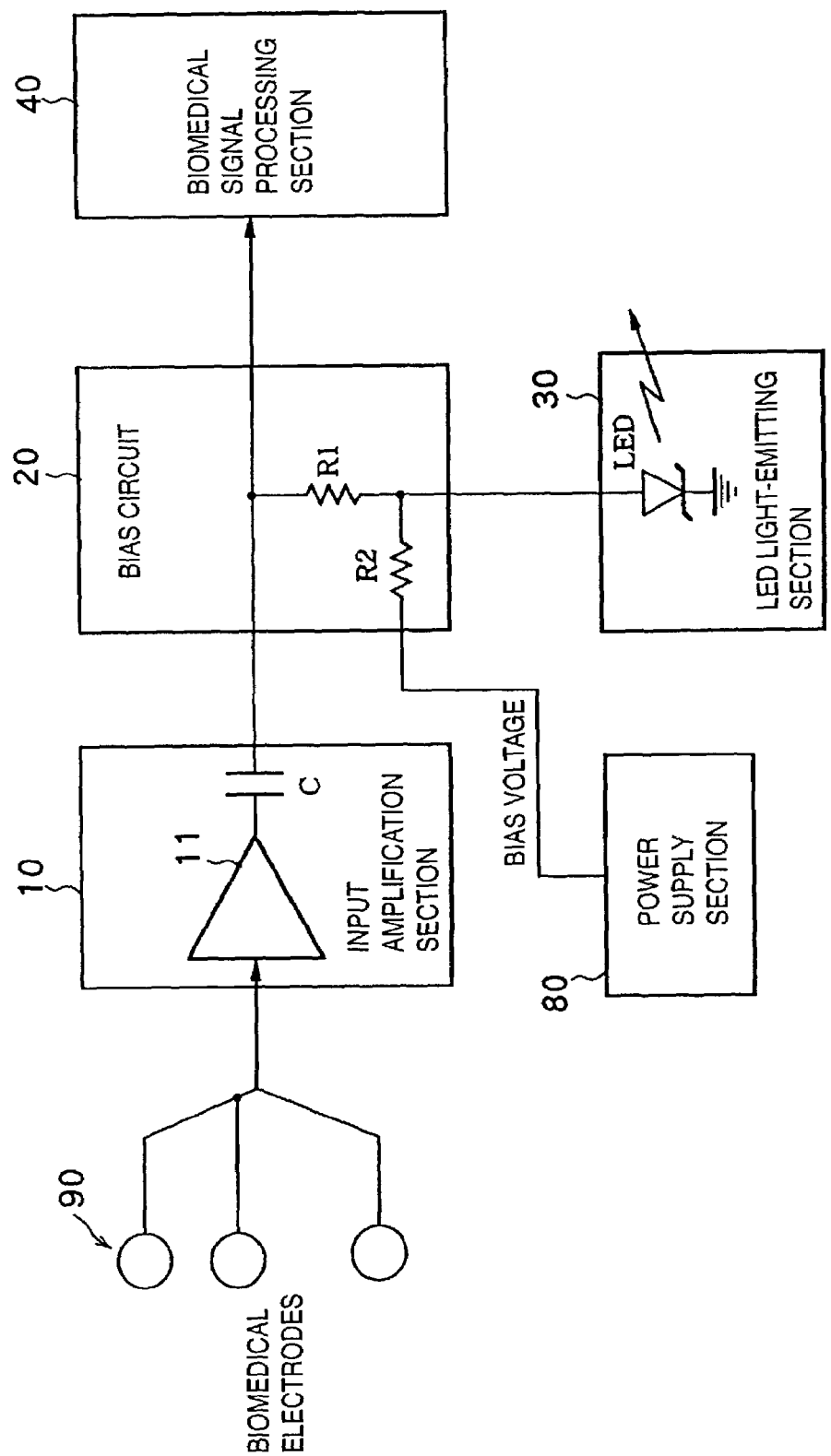
FIG. 2 is a circuit diagram illustrating a detailed configuration of a bias circuit and an LED light-emitting section specific to this embodiment.

Of the medical telemetery apparatus in the above described configuration, detailed configurations of the bias circuit 20 and LED light-emitting section 30, which are specific to this embodiment will be explained with reference to FIG. 2. FIG. 2 is a circuit diagram illustrating a detailed configuration of the bias circuit 20 and the LED light-emitting section 30 according to this embodiment.

In FIG. 2, collected biomedical signals from the biomedical electrodes 90 are input to an electrocardiogram amplifier 11 of the input amplification section 10, where the collected biomedical signals are amplified to an electrocardiogram signal of a predetermined level. The output from this electrocardiogram amplifier 11 is input to the bias circuit 20 through a capacitor C that prevents backflow of the DC component to the electrocardiogram amplifier 11.

The bias circuit 20 supplies the signal from the input amplification section 10 to the biomedical signal processing section 40 as it is and at the same time supplies the signal to one terminal of an LED light-emitting element (LED) whose other terminal is grounded, making up the LED light-emitting section 30 through a resistor R1.

The present invention is constructed in such a way that the bias voltage from the power supply section 80 is applied to the signal supplied to the one terminal of this LED light-emitting section 30 through a resistor R2 and a predetermined bias voltage is superimposed on the connection between the resistor R1 and LED 30. In this embodiment, the level of this bias voltage is controlled to a voltage level which becomes a positive potential (intermediate luminescence intensity) when electrocardiogram signals are input to the input amplification section 10 and the level of the minimum voltage supplied to the connection between the resistor R1 and LED light-emitting element is a normal waveform.

Figure 3:
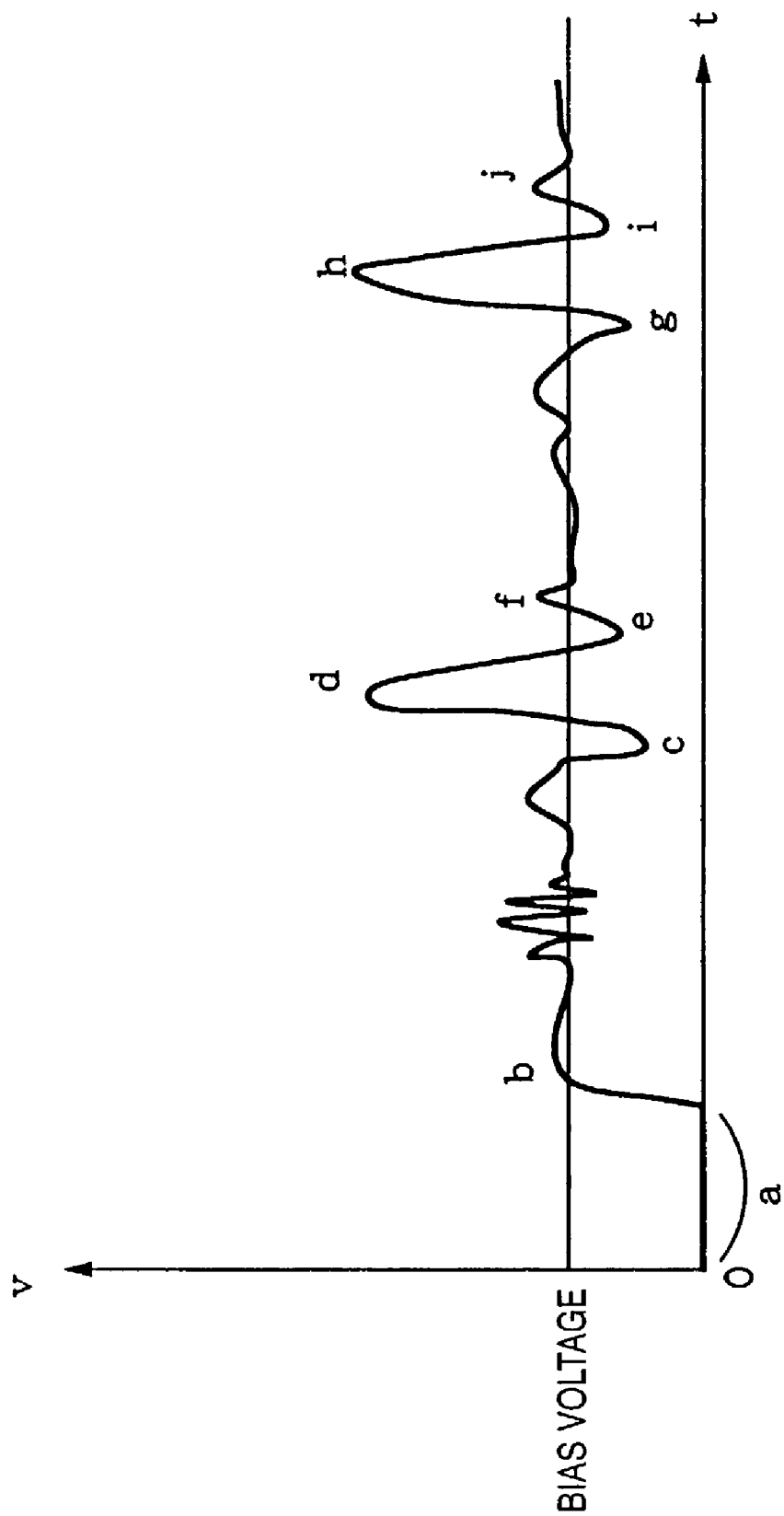
FIG. 3 is a timing chart illustrating a light-emitting control of the light-emitting section of this embodiment.

An example state of a voltage applied to the light-emitting section 30 (drive voltage of the light-emitting section 30) of this embodiment in the above described configuration is shown in FIG. 3. FIG. 3 is a timing chart illustrating an example state of a voltage applied to the light-emitting section 30 (drive voltage of the light-emitting section 30) of this embodiment.

Before power is supplied to the medical telemetery apparatus of this embodiment, no drive power is supplied to the LED light-emitting section 30, which prevents the LED light-emitting section 30 from emitting light. This state is the period indicated by a reference character a in FIG. 3.

Thus, when the LED light-emitting section 30 is not emitting light, it is possible to visually confirm that no drive power is supplied to the apparatus. Also when the drive battery of the medical telemetery apparatus is exhausted and its power supply is reduced, the amount of light emission of the LED light-emitting section 30 remains low all the time, and therefore it is possible to identify any defect of the power supply section 80 from the light-emitting state of the LED light-emitting section 30.

Then, when power is supplied, the light-emitting state changes to the state indicated by a reference character b in FIG. 3 and the voltage supplied to the LED light-emitting section 30 is the bias voltage while the power supply section 80 is operating normally. Accordingly, when there is no input and the power is simply kept ON, the LED light-emitting section is in a half light-emitting state (light emission with intermediate intensity), which is a light-emitting state by the bias voltage. Therefore, when the LED light-emitting section is in a half light-emitting state, it is possible to visually confirm that no collected electrocardiogram signals, etc. are input from the biomedical electrodes 90 though power is supplied to the apparatus.

When the electrocardiogram signals are input from the biomedical electrodes 90 to the input amplification section 10 in this state, the supply voltage to the LED light-emitting section 30 changes, for example, as indicated by reference characters c, d, e and f in FIG. 3. The state indicated by c in FIG. 3 is a state in which the supply voltage to the LED light-emitting section 30 is reduced and the luminescence intensity weakens. On the contrary, the state indicated by d in FIG. 3 is a state in which the supply voltage to the LED light-emitting section 30 increases significantly and the luminescence intensity increases.

Likewise, the state indicated by e in FIG. 3 is a state in which the supply voltage to the LED light-emitting section 30 is reduced slightly and the luminescence intensity weakens slightly. On the contrary, the state indicated by f in FIG. 3 is a state in which the supply voltage to the LED light-emitting section 30 increases slightly and the luminescence intensity increases slightly. The same applies to reference characters g, h, i and j in FIG. 3.

As a result, while the electrocardiogram signals are input, the LED light-emitting section 30 alternates between a weak light-emitting state and a strong light-emitting state, and the luminescence intensity changes. Therefore, if this light-emitting state can be confirmed, it is possible to visually confirm that the electrodes 90 are correctly attached and that the electrocardiogram signals are also being collected normally.

Adopting the above described configuration makes it possible to implement, using only one LED light-emitting element, a power supply lamp for identification as to whether power is ON or OFF and a display device for confirmation as to whether the bioelectrical signal is normally collected or not, both of which are necessary in prior arts. This simplifies the configuration and also reduces power consumption required for the display.

Furthermore, even when the apparatus fails to operate normally under certain circumstances, it is possible to easily check it by simply visually inspecting the light-emitting state of the LED light-emitting element.

By the way, in the above examples, the case where the power supply display lamp and the electrocardiogram collection state display device are implemented by the LED-display section 30 has been explained, but it is also possible to provide a power supply lamp separately and use the LED display section 30 in FIG. 2 only for confirmation of its biomedical signal collection state. In this case, it is possible to further suppress the bias voltage to a lower value and keep the LED display section almost unlit when no signal arrives.

As described above, the present invention makes it possible to reliably visually confirm the state of connection of the detection section for detecting biomedical signals to the examinee and the operating state of the apparatus using only the own apparatus with a simple configuration and without the necessity for confirmation, etc. using other special devices.

Furthermore, it is also possible to check the state of the drive power supply and the operating state of the apparatus together.

Furthermore, the present invention can be applied to the system comprising either a plurality of units or a single unit. It is needless to say that the present invention can be applied to the case which can be attained by supplying programs which execute the process defined by the present system or invention.

What is claimed is:

1. A biomedical signal processor comprising:
   a power supply section that supplies drive power to the apparatus;
   an input amplification section that takes in and amplifies biomedical signals from a detection section that detects those biomedical signals;
   bias means for applying a predetermined bias voltage to an output signal from said input amplification section; and
   light-emitting means for emitting light with intensity corresponding to the biomeidcal signals to which said bias means applies the predetermined bias voltage,
   wherein it is possible to simultaneously recognize an operating condition of said power supply section and a detection condition of said detection section from a luminescence intensity of said light-emitting means.

2. The biomedical signal processor according to claim 1, wherein said biomedical signals are used as electrocardiogram signals and said detection section is used as an electrocardiogram electrode, and said bias means applies a bias voltage so that the luminescence intensity of said light-emitting means becomes intermediate luminescence intensity when no electrocardiogram signal is detected from said input amplification section.

3. A method of controlling a biomedical signal processor provided with an input amplification section that takes in and amplifies biomedical signals from a detection section that detects those biomedical signals and light-emitting means, comprising the steps of:
   amplifying an input signal at said input amplification section;
   adding a predetermined bias voltage thereto; and
   letting said light-emitting means emit light with intensity corresponding to the biomedical signals with said bias voltage added,
   wherein it is possible to simultaneously recognize the operating condition of the power supply section and the detection condition of the detection section from the light-emitting state of said light-emitting means.

4. The method of controlling a biomedical signal processor according to claim 3, wherein said biomedical signals are used as electrocardiogram signals and said detection section is used as an electrocardiogram electrode, and a bias voltage is applied so that the luminescence intensity of said light-emitting means becomes intermediate luminescence intensity when no electrocardiogram signal is detected from said input amplification section.

* * * * *